(12) United States Patent
Bronstein et al.

(10) Patent No.: US 6,243,980 B1
(45) Date of Patent: Jun. 12, 2001

(54) PROTEASE INHIBITOR ASSAY

(75) Inventors: Irena Bronstein, Newton; John Voyta, Sudbury; Michelle Palmer, Arlington; Bonnie Tillotson, Belmont, all of MA (US)

(73) Assignee: Tropix, Inc., Bedford, MA (US)

( * ) Notice: Subject to any disclaimer, the term of this patent is extended or adjusted under 35 U.S.C. 154(b) by 0 days.

(21) Appl. No.: 09/035,820

(22) Filed: Mar. 6, 1998

Related U.S. Application Data

(60) Provisional application No. 60/038,940, filed on Mar. 7, 1997.

(51) Int. Cl.$^7$ ............... G01N 33/533; G01N 33/573; G01N 33/535

(52) U.S. Cl. ............... 43/7.72; 435/6; 435/7.1; 435/7.2; 435/7.23; 435/7.5; 435/7.72; 435/7.8; 435/7.92; 435/23; 435/24; 435/184; 435/219; 436/172; 436/800; 436/805; 436/537

(58) Field of Search ............... 435/6, 7.1, 7.2, 435/7.23, 7.5, 7.72, 7.9, 7.82, 12, 15, 16, 17, 18, 19, 20, 21, 23, 24, 184, 537; 530/330, 331, 807, 333; 436/173, 800, 805, 820, 219

(56) References Cited

U.S. PATENT DOCUMENTS

| | | | |
|---|---|---|---|
| 4,716,109 | * 12/1987 | Baker et al. | 435/7 |
| 4,931,223 | 6/1990 | Bronstein et al. . | |
| 4,952,707 | 8/1990 | Edwards et al. . | |
| 4,956,477 | 9/1990 | Bronstein et al. . | |
| 4,978,614 | 12/1990 | Bronstein . | |
| 5,089,630 | 2/1992 | Bronstein et al. . | |
| 5,112,960 | 5/1992 | Bronstein et al. . | |
| 5,145,772 | 9/1992 | Voyta et al. . | |

(List continued on next page.)

OTHER PUBLICATIONS

Ayyagari, M.S., et al. Chemiluminescence–Based Inhibition Kinetics Of Alkaline Phosphatase In The Development Of A Pesticide Biosensor, Biotechnol. Prog. 1995, vol. 11, pp. 699–703.

(List continued on next page.)

Primary Examiner—Mary E. Ceperley
Assistant Examiner—Gailene R. Gabel
(74) Attorney, Agent, or Firm—Piper Marbury Rudnick & Wolfe LLP; Steven B. Kelber

(57) ABSTRACT

Heterogenous and homogenous assays are provided for the detection of protease inhibitory activity in a sample or target compound, taking advantage of the chemiluminescent characteristics of 1,2-dioxetanes. In the heterogenous assay, a peptide bearing a cleavage site for the protease of interest is provided with a first member of a first ligand binding pair at one end, and a first member of a second ligand binding pair at the other end. The other member of the first ligand binding pair is attached to a surface, which binds the peptide, or protease substrate, to the surface. The peptide substrate is combined with the protease and target compound or sample. Substrate cleavage, if not inhibited, is allowed to occur, and any unbound cleaved fragments are removed. An enzyme complexed with the second member of the second ligand binding pair is added, and allowed to bind to any of the (uncleaved) first member of the second ligand binding pair remaining. Unbound complex is removed, and a 1,2-dioxetane substrate for the enzyme is added. If any peptide substrate has not been cleaved, the dioxetane will chemiluminesce, indicating inhibitory activity. In a homogenous assay, the same substrate bears at one end a fluorescent energy accepting moiety, and at the other end a 1,2-dioxetane or precursor. If the substrate is cleaved by the protease, the dioxetane and the fluorescent moiety are not in close physical relationship, and no energy transfer occurs when the dioxetane is caused to decompose. If cleavage has not occurred, indicating inhibition, when the dioxetane is caused to decompose, energy is transferred to the fluorescing entity, which releases light of a wavelength recognizably distinct from that of the dioxetane.

14 Claims, 16 Drawing Sheets

U.S. PATENT DOCUMENTS

| | | |
|---|---|---|
| 5,220,005 | 6/1993 | Bronstein . |
| 5,326,882 | 7/1994 | Bronstein et al. . |
| 5,330,900 | 7/1994 | Bronstein et al. . |
| 5,538,847 | 7/1996 | Bronstein et al. . |
| 5,543,295 | 8/1996 | Bronstein et al. . |
| 5,547,836 | 8/1996 | Bronstein et al. . |
| 5,591,591 | 1/1997 | Bronstein et al. . |
| 5,593,828 | 1/1997 | Bronstein et al. . |
| 5,605,795 | 2/1997 | Bronstein . |
| 5,637,747 | 6/1997 | Bronstein et al. . |
| 5,654,154 | 8/1997 | Bronstein et al. . |
| 5,679,803 | 10/1997 | Bronstein et al. . |
| 5,726,025 * | 3/1998 | Kirschner et al. ............... 435/7.2 |
| 5,753,436 | 5/1998 | Bronstein et al. . |
| 5,786,198 * | 7/1998 | Kraus et al. .................. 435/236 |

OTHER PUBLICATIONS

Matayoshi, E.D., et al. Novel Fluorogenic Substrates For Assaying Retroviral Proteases By Resonance Energy Transfer. Science. Feb. 23, 1990, vol. 247, pp. 954–958.

* cited by examiner

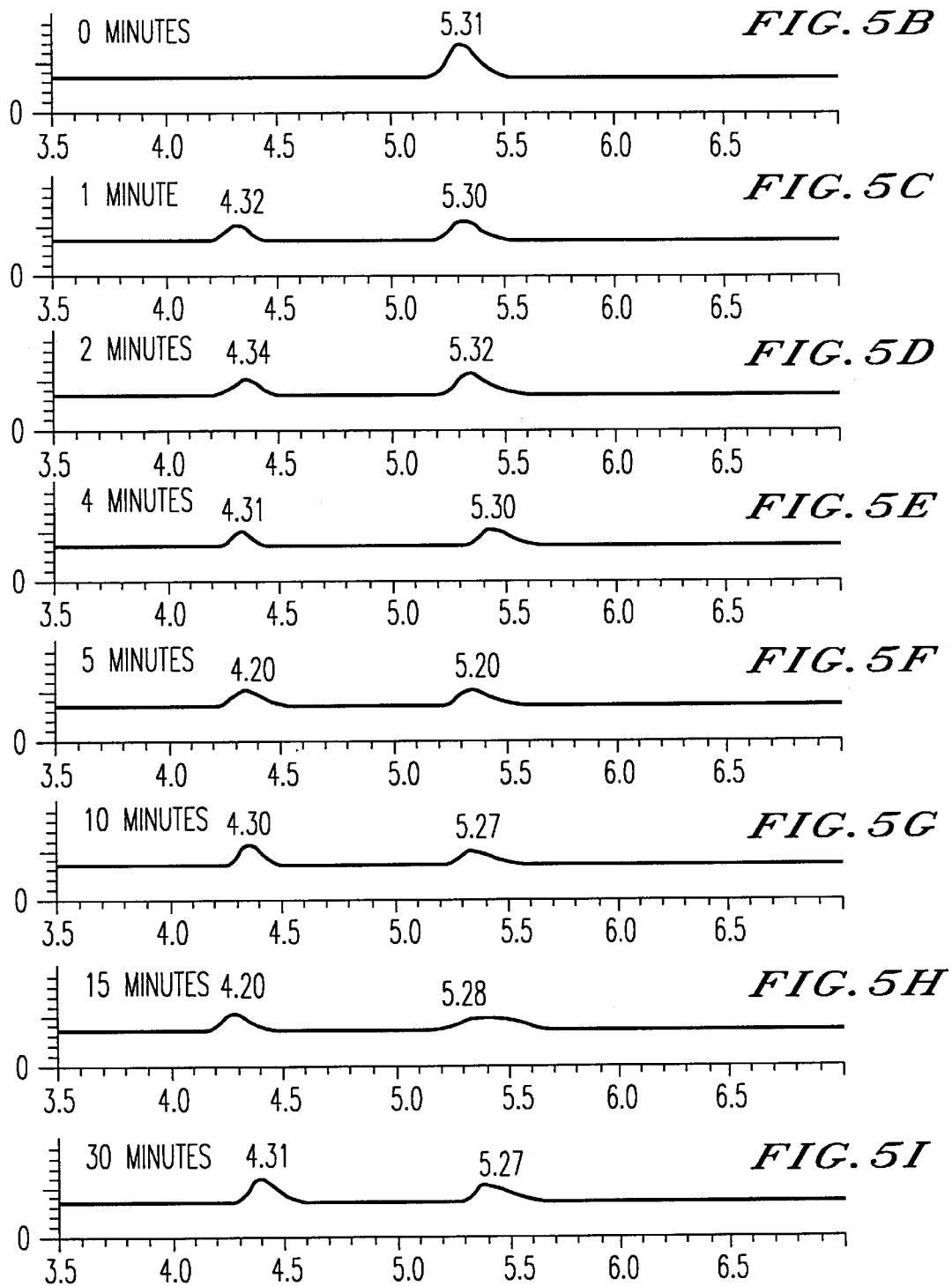

PROTEASE INHIBITOR ASSAY

This application is a regular National application claiming priority from Provisional Application, U.S. Application Ser. No. 60/038,940 filed Mar. 7, 1997, now abandoned.

BACKGROUND OF THE INVENTION

1. Field of the Invention

This invention pertains to the use of chemiluminescent 1,2-dioxetanes in homogenous or heterogeneous assays to detect proteases inhibitors.

2. Discussion of the Background

The identification of novel therapeutics that block or inhibit inimical proteases, or proteases that mediate disease conditions, such as the 11-kd protease encoded by the human immunodeficiency virus 1(HIV-1) is a key step in slowing the disease process of AIDS. Retroviral proteases are essential in the process of viral gag-pol polyproteins of the HIV-1 and HIV-2 viruses. There are a few highly conserved consensus sequences in retroviral polyproteins, one of which consists of a pentapeptide (Ser/Thr)-X-X'-(Tyr/Phe)-Pro (SEQ ID No:1). Cleavage occurs between the Tyr or Phe and Pro residues. Blocking activity of these proteases will interfere with the progression of HIV infection. Although potent drugs which block HIV protease activity have been found, there is an ongoing need to find and develop novel inhibitors.

Current methods utilized in rapid screening of protease inhibitors are subject to many interferences from a variety of sources. The most common non-isotopic approach is a fluorescent assay. In one case, such as in the detection of HIV protease, the fluorescent substrate is labeled with a fluorescent dansyl group on one end of a peptide and a quencher on the other. An increase in fluorescence signal occurs upon cleavage of the protease due to the fact that the emitter and the quencher are separated as described in Matayoshi et al., 1990, Science 247: 954–958. Fluorescent substrates for other proteases can be designed with a terminal fluorophore which emits a fluorescent signal upon cleavage by the enzyme.

Both of the above assay approaches are commonly used as high throughput assays for screening large chemical, natural product and combinatorial libraries. These assays tend to have problems related to autofluorescence of biological components due to the nature of the molecules which are screened. Many of the compounds and natural product extracts are colored or fluorescent and are present in the solution when the assay signal is monitored. This results in an assay interference which limits the detection sensitivity and the dynamic range of the assay. This interference can easily be interpreted as an inhibition of the enzyme, making it difficult to determine true positive inhibition, thus, requiring extensive follow-up assays to distinguish true positives from the false positives.

U.S. Pat. No. 5,591,591, assigned to Tropix, describes assays for the detection of proteases wherein a dioxetane compound bearing a proteolytic enzyme-specific amino acid or peptide, is added to a sample suspected of containing the protease, and the amino acid is removed by enzymatic reaction by the protease, causing the dioxetane to decompose and chemiluminescence.

SUMMARY OF THE INVENTION

An alternative approach to the above homogeneous approaches is to use homogenous or heterogeneous assays which are not subject to interference. The present inventors have developed highly sensitive assays using a chemiluminescent 1,2-dioxetane substrate for high throughput screening of HIV-1 protease activity. The present invention provides the advantage of an assay that it is not subject to interferences from colored or fluorescent compounds, and therefore is more sensitive and exhibits a greater dynamic range compared to a direct, fluorescent enzyme assay. This assay, adapted for the detection of HIV protease inhibitors, utilizes a synthetic peptide substrate I (Fam-spacer-Ser-Gln-Asn-Tyr-Pro-Ile-Val-Gln-spacer-(Biotin)-NH2) (SEQ ID No:2) whose sequence is derived from the native cleavage site of the Gag polyprotein. (Fam is used herein to indicate fluorescein). Many high throughput HIV screening methodologies exist which utilize large quantities of reagents and involve more laborious manipulations. The assay of the present invention may be advantageously formatted as a simple single plate endpoint assay which is sensitive down to fmoles of captured peptide which is particularly useful for high throughout screening, although it may also be presented as a conventional two-step transfer and dilation capture assay. The assay uses a chemiluminescent 1,2-dioxetane alkaline phosphatase substrate in an immunoassay format for the sensitive detection of cleaved peptide. The uncleaved peptide is recognized by an anti-fluorescein alkaline phosphatase conjugated antibody. Capture conditions have been optimized to assure a linear response to cleaved peptide concentration. This response correlates well to HPLC analysis of cleaved product. The HIV assay has been validated for acetyl-pepstatin, a known HIV-1 inhibitor. This robust assay is amenable to automation and can be used to screen large numbers of compounds in a cost effective 96 well format.

In an alternative embodiment, a homogenous assay less sensitive to color or fluorescence interference than prior art assays is used. In this assay, the same peptide is employed, but labeled at one terminus with fluorescein or other fluorescing energy acceptor, and at the other end by a 1,2-dioxetane label covalently attached to the peptide terminus. After admixture of the target compound, the dioxetane is caused to decompose by addition of a chemical (enzymatic or non-enzymatic) or another trigger, such as application of heat or change in pH. If the peptide has not been cleaved, the dioxetane is in close physical relationship with the fluorescent energy acceptor, and upon triggering, energy transfer assisted fluorescence is observed. The light has a characteristic color dependent on the fluorescent emitter, such as green for fluorescein. If the peptide has been cleaved, the chemiluminescent light of the dioxetane itself, typically a bluer light, is observed.

BRIEF DESCRIPTION OF THE DRAWINGS

FIG. 12. Titration of rec HIV-1 Protease I with 100 nM HIV FLAG Peptide. Diluted rec HIV-1 protease was added to 100 nM HIV FLAG peptide in protease buffer. Reactions were done either in eppendorf tubes or directly in wells precoated with Anti-FLAG MI monoclonal antibody (0.1 ug/ml). Competing FLAG octapeptide at 2.5 uM was added to control tubes and wells. Incubations were done for 1 hour at 37° C., then eppendorf reaction products transferred to wells, and further incubated for 1 hour at room temp. Plates were washed 3x in PBS/Tween/CaCl buffer followed with addition of a 1:20,000 dilution of Avidix-AP. Plates were further incubated for 1 hour at room temp and then washed 3x with PBS/Tween/CaCl buffer and 1x with Tris/MgCl/CaCl pH 9.8 buffer. 100 ul CSPD/Sapphire II was added and wells incubated for 30 minutes to room temp. Luminescence was then measured in a TR717 microplate luminometer (Tropix).

DESCRIPTION OF THE PREFERRED EMBODIMENTS

Figure 1:
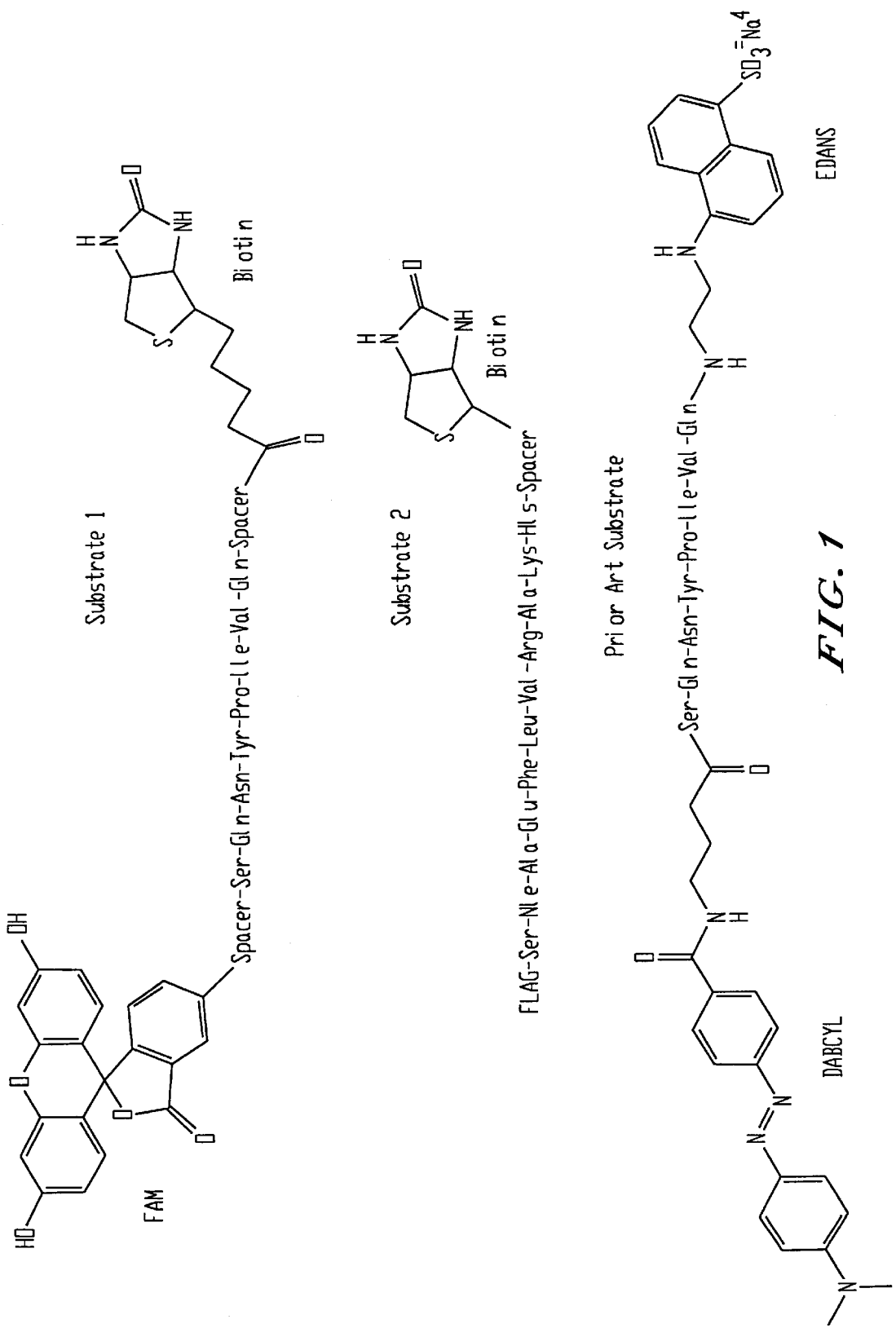
FIG. 1. Illustration of two labeled HIV-1 substrates I and II whose sequences are derived from a natural processing site for aspartyl HIV-1 protease. Incubation of these two HIV-1 peptides (SEQ ID No:2–3) with rec HIV-1 protease results in a specific cleavage between the Try-Pro bond as reported in Kohl, NE et al.(1988), Proc. Acad. Sci. USA, 85, 4684 and Billich, SW, et al. (1988), J. Biol. Chem. 263, 17905. These are compared against the prior art substrate as reported in Mayatoshi et al (SEQ ID No:4).
Figure 2A:
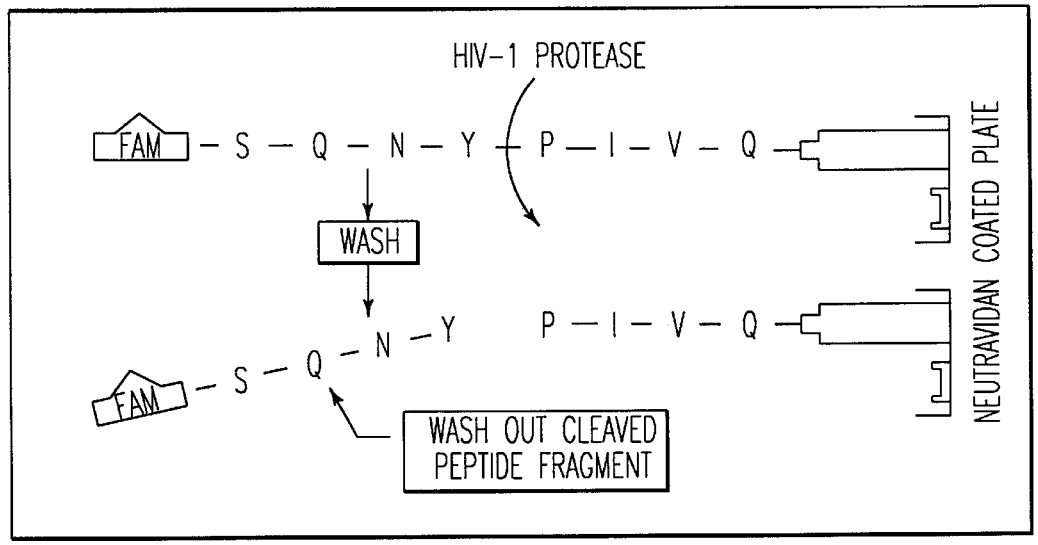
FIG. 2. HIV-1 Protease Assay. Steps include 1. Addition of rec HIV-1 protease, acetyl-pepstatin(3) and/or screening compound to NeutrAvidin coated plates, with a preincubation. 2. Addition of HIV-1 protease peptide 1 (SEQ ID No:2) followed with a 60 min. incubation at 37° C. 3. Wash out cleaved peptide fragment. 4. Add anti-fluorescein alkaline phosphatase antibody to detect uncleaved bound peptide and then 5. Add CSPD/Sapphire II and measure emitted light in a TR717 luminometer(Tropix).
Figure 2B:
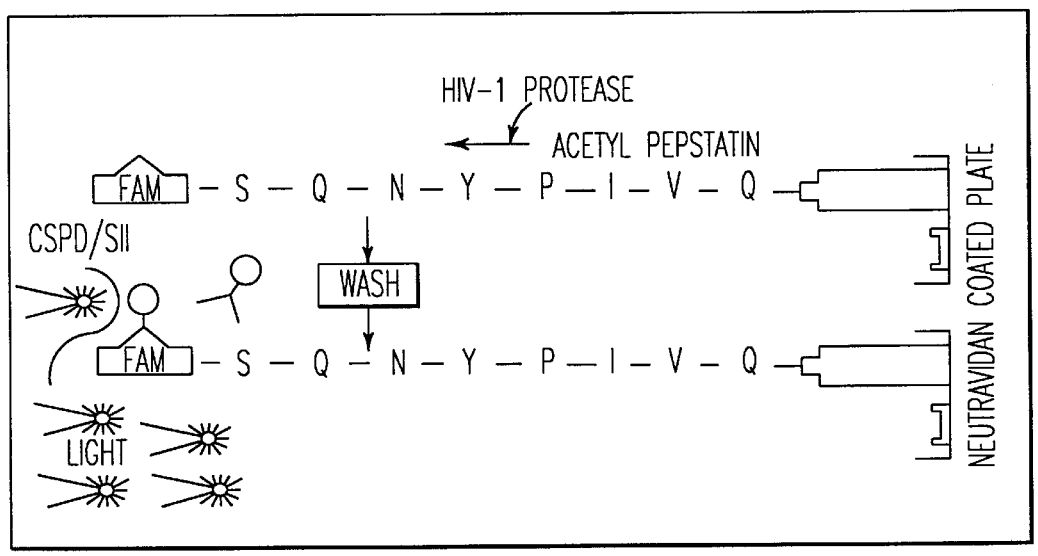
Figure 3:
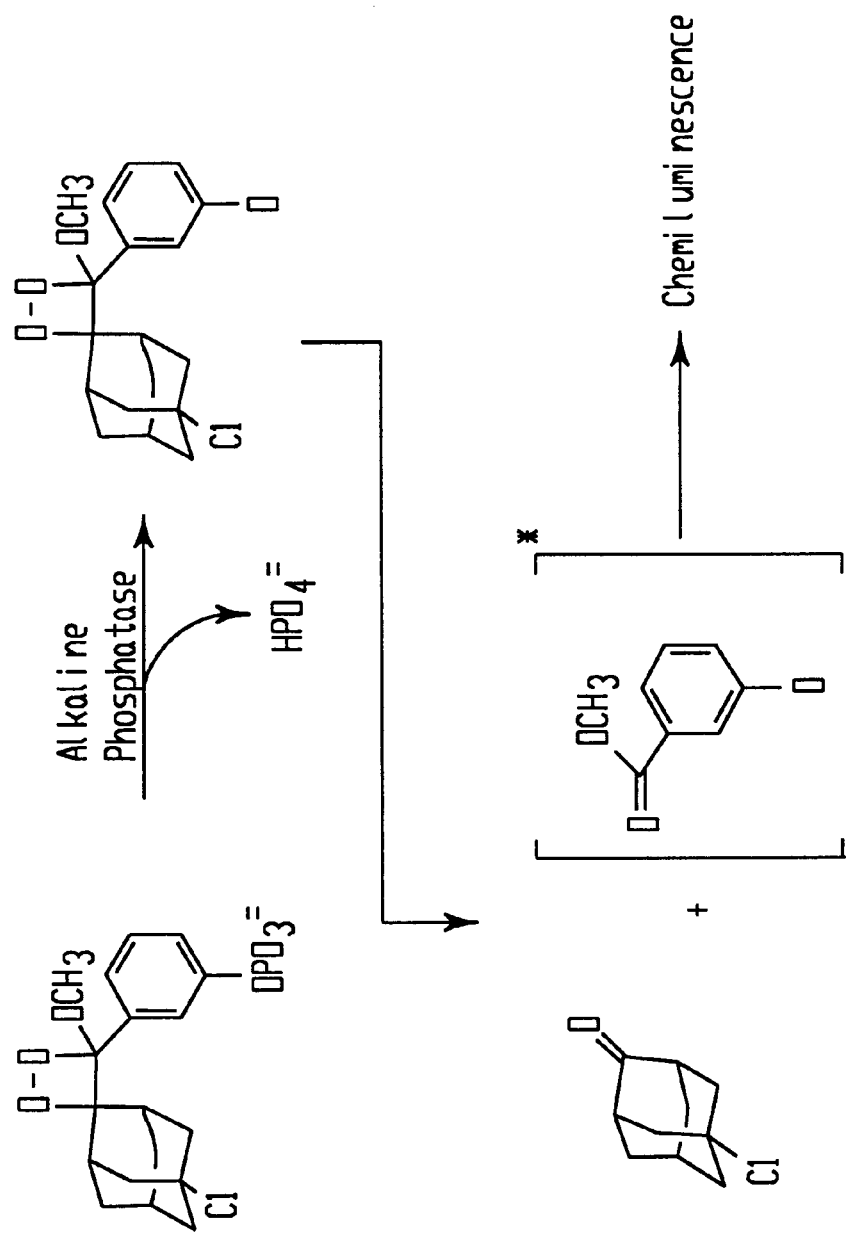
FIG. 3. The phosphate group on the CSPD substrate is cleaved by alkaline phosphatase to generate the unstable anion intermediate 1. Intermediate 1 then undergoes decomposition producing a long-lived emission at 470 nm.
Figure 4:
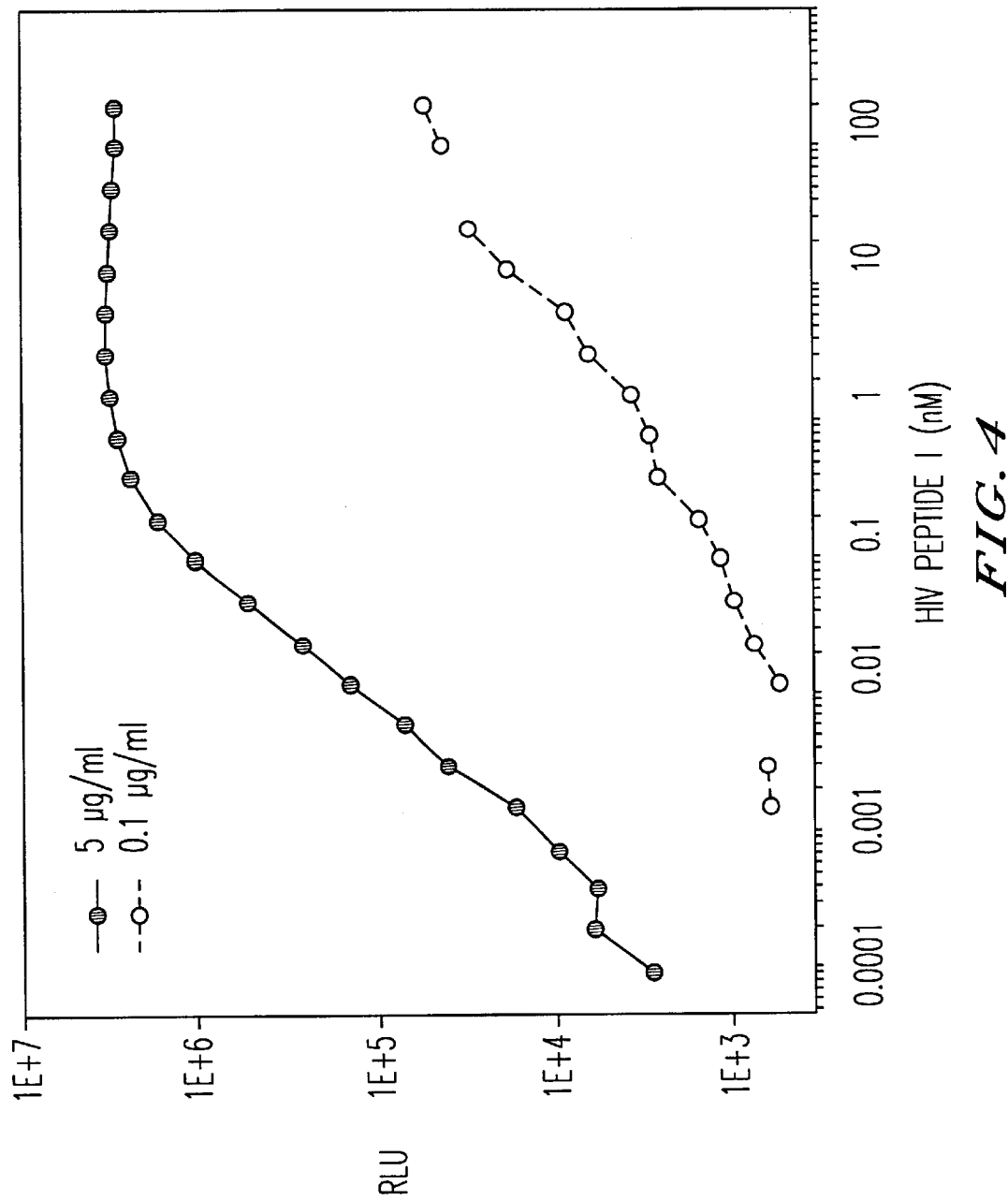
FIG. 4. HIV-1 protease peptide I titration on Neutravidin coated plates. 100 ul of diluted peptide was added to various densities of coated Neutravidin wells. Plates were washed and peptide was detected with an anti-fluorescein alkaline phosphatase conjugate followed with the addition of CSPD/Sapphire II. Light emission was measured in a TR717 microplate luminometer(Tropix).
Figure 5A:
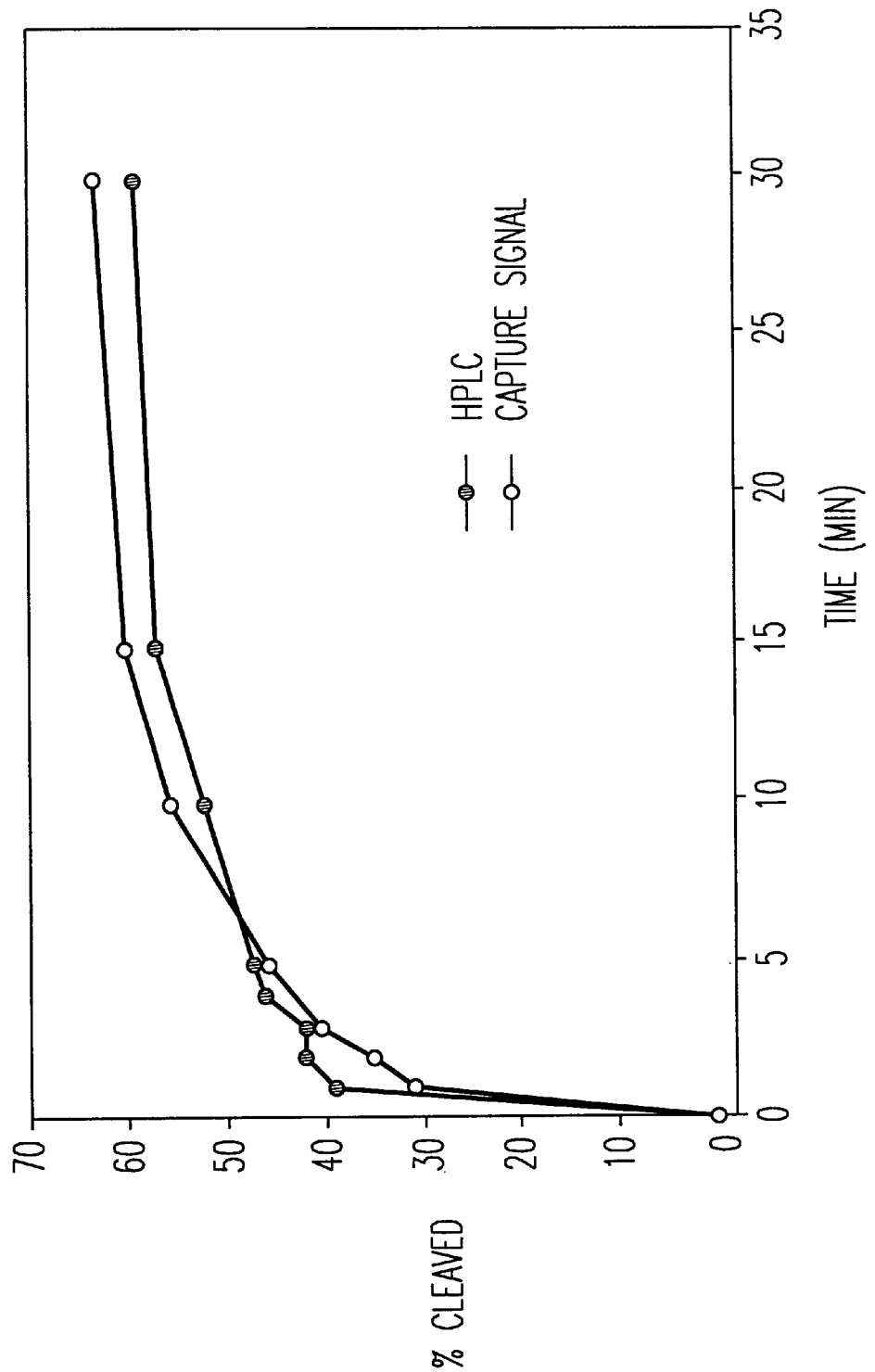
FIG. 5(A&B). Comparison of HIV-1 peptide I cleavage by rec HIV-1 protease by HPLC analysis and capture on Neutravidin coated plates. 35 nM of rec HIV-1 protease was added to 10 uM HIV peptide in eppendorf tubes and incubated at 37° C. At specific time points 0. 1% TFA was added to stop the reaction and tubes placed on ice. Reaction products were analyzed by HPLC. Injection volumes were 100 ul and absorbency was monitored @ 490 nm. The percentage of cleaved product was calculated from the peak areas. For peptide capture experiments, 100 ul of a 1:50 dilution was added to Neutravidin (5 ug/ml) coated plates and incubated at ambient temp. for 60 min. after a wash step, captured peptide was detected with anti-fluorescein conjugated alkaline phosphatase antibody followed by another wash step and then the addition of CSPD/Sapphire II. Light emission was measured in a TR717 microplate luminometer (Tropix).

A peptide substrate is synthesized which contains the appropriate cleavage site for the target protease. This peptide is labeled, in a heterogenous assay, with one member of a first ligand binding pair, such as biotin, on one end and a member of a second ligand binding pair, such as fluorescein, at the other end. This peptide is then incubated with the protease and a compound of interest to be screened for inhibitory activity, in a well or other solid phase coated with the second binding ligand of said first ligand binding pair, such as avidin or strepavidin.

The spacer between the ligand binding pair members and the peptide of the inventive substrate may be a covalent bond or any covalent binding moiety which does not interfere with either the first or second ligand binding pair or substrate cleavage. Among exemplary sequences are C1–12 alkyls, alkylamino's, carboxylic acids, or any neutral moiety terminating in coupling functionalities at either end. The spacer may be provided with water-solubility enhancing substituents (e.g., carboxy, sulfoxy, halo, etc.) or, where necessary for enzyme/antibody presentation, to cyclize the substrate, bridging agents.

After incubation, the wells are washed, incubated with the second binding member of said second binding ligand pair conjugated with an enzyme which is an effective trigger for a 1,2-dioxetane, such as alkaline phosphatase, washed, incubated with a 1,2-dioxetane substrate such as chlorine substituted phosphate dioxetane (CSPD) and the signal is measured. Higher signals are detected in the presence of an inhibitor.

The 1,2-dioxetanes used as substrates may be any of those described in any of Tropix' prior patents, including 4,931,223; 4,931,569; 4,952,707; 4,956,477; 4,978,614; 5,032,381; 5,112,960, 5,154,772; 5,220,005; 5,225,584; 5,326,882; 5,330,900; 5,336,596; 5,543,295; 5,582,980; 5,605,795; 5,625,007; 5,654,154; and 5,679,803, which are incorporated by reference herein. The above mentioned patents disclose 1,2-dioxetanes as chemiluminescent compounds which can be used as reporter molecules in ultrasensitive assays that can be conducted quickly without resort to exotic conditions or elaborate apparatus, for the detection of a variety of biological molecules. A preferred substrate is CSPD, the chlorine-substituted counterpart of AMPPD, which is the disodium salt of 3-(4-methoxy-spiro[1,2-dioxetane-3,2'-tricyclo[$3.3.1.1^{3,7}$]decan]4-yl)phenyl phosphate.

The dioxetanes contain a fluorescent chromophore group, preferably an aryl group such as phenyl or naphthyl and an enzyme cleavable group, e.g., a phosphate ester, which when cleaved by the appropriate enzyme, e.g., alkaline phosphatase, forms a negatively charged substituent (e.g., an oxyanion). This destabilizes the dioxetane, thereby causing the dioxetane to decompose to form two carbonyl-containing groups accompanied by the release of light.

To enhance the chemiluminescent signal, and improve signal/noise ratio to permit discrimination between background signals and positive target-responsive signals at very low levels, a water-soluble enhancement agent may be added to the sample prior to or concomitant with the introduction of the dioxetane. Specific enhancement agents which may be used include: quaternary onium polymeric salts such as polyvinylbenzyltributyl-ammonium chloride (Sapphire II, Tropix) or any of those disclosed in U.S. Pat. No. 0 5,336,596 as potential membrane coatings, neutral detergents such as Tween-20 (Sigma), cationic detergents, such as cetyltrimethylammonium chloride (CTAB, Sigma) and combinations thereof.

Families of proteolytic enzymes which may be targets for determination of inhibitory agents include
Cysteine Proteases
Caspases 1, 2, 3, 6, 7, 8
Cathepsins (B, H, S and L)
Hydrolase
L-proteinases
Calpain
Interleukin converting proteases (ICE)
Serine Proteases
Urokinase
Trypsin
Thrombin
Cathepsin G
Aspartic Proteases
HIV-1 and 2
Yapsin I and YAP 3
Plasmepsin I and II
Cathepsin D and E
Metalloproteinases
Collagenase
Gelatinase A and B
Stromelysin
Aminopeptidase
Elastase
or any of those mentioned in U.S. Pat. No. 5,591,591. Assay conditions and applications for specific proteases are also listed in U.S. Pat. No. 5,591,591. It is possible to use any peptide which is recognized by the protease of interest. Examples of specific peptides and proteases are listed in U.S. Pat. No. 5,591,591. In particular, a peptide is prepared which features a cleavage site for which the target protease is specific. The resulting peptide is short, and easily prepared using conventional synthetic technology.

A large variety of ligand binding pairs can be used for both the first and second ligand binding pair employed. Among preferred labels for either end of the peptide are: Biotin, Fluorescein (FAM), FLAG, HIS tag (6 histidine amino acid sequence), and Digoxin (digoxigenin labeled peptide). These are bound by the other member of the first pair, preferably bound or attached to a solid phase so as to remain through washing and addition of the other member of the second pair, added after an opportunity for cleavage to occur, the other member being complexed with alkaline phosphatase or other suitable enzyme as a trigger. The principal restriction on the identity of the binding pairs is that the first binding pair be distinct from, and not interact with, the second binding pair.

In addition to alkaline phosphatase, other enzymes which may be used to cleave the enzymatically cleavable group from the dioxetane include: acid phosphatases, esterases, decarboxylases, phospholipase D, β-xylosidase, β-D-frucosidase, thioglucosidase, β-D-galactosidase, α-D-galactosidase, α-D-glucosidase, β-D-glucosidase, α-D-mannosidase, β-D-mannosidase, β-D-fructofuranoside, β-D-glucosiduronase, and trypsin.

In addition to being of particular interest as organic moieties that constitute diagnostic markers, protease enzymes are also of considerable interest as enzyme labels.

Examples of diagnostic protease markers include cathepsin B (cancer), cathepsin G (emphysema, rheumatoid arthritis, inflammation), plasminogen activator (thrombosis, chronic inflammation, cancer) and urokinase (cancer). Assays for protease detection are therefore needed to monitor protein stability in various biological and commercial processes.

In an alternative embodiment of this assay a homogeneous chemiluminescent energy transfer assay is provided. In this approach, one end of the cleavage sequence peptide bears a 1,2-dioxetane or dioxetane precursor. Direct attachment of this moiety, followed by oxygenation to form the dioxetane, is enabled in U.S. patent application Ser. No. 08/767,479, allowed and incorporated herein by reference. The other end of this peptide bears an energy accepting fluorescent molecule such as fluorescein, or any of a variety of similar fluorescing moieties, such as those disclosed in U.S Pat. No. 5,004,565 and 5,208,148 which are incorporated herein by reference. The peptide is sufficiently short (no more than about 10 amino acid residues) such that the dioxetane is in close physical association with the fluorescent label. Upon triggering of the dioxetane, which can be effected by addition of an enzyme, or pH alteration, or application of heat or other triggers, the dioxetane decomposes, emitting energy which excites the fluorescent moiety which then fluoresces if no cleavage has occurred (a positive test for protease inhibition). If cleavage has occurred, the dioxetane and fluorescent moieties are no longer in close physical relationship, and the light is emitted by the chemiluminescent dioxetane. The wavelength of the fluorescent emitter is characteristically shifted markedly from that of the dioxetane, allowing easy discrimination in a homogenous assay.

Figure 14A:
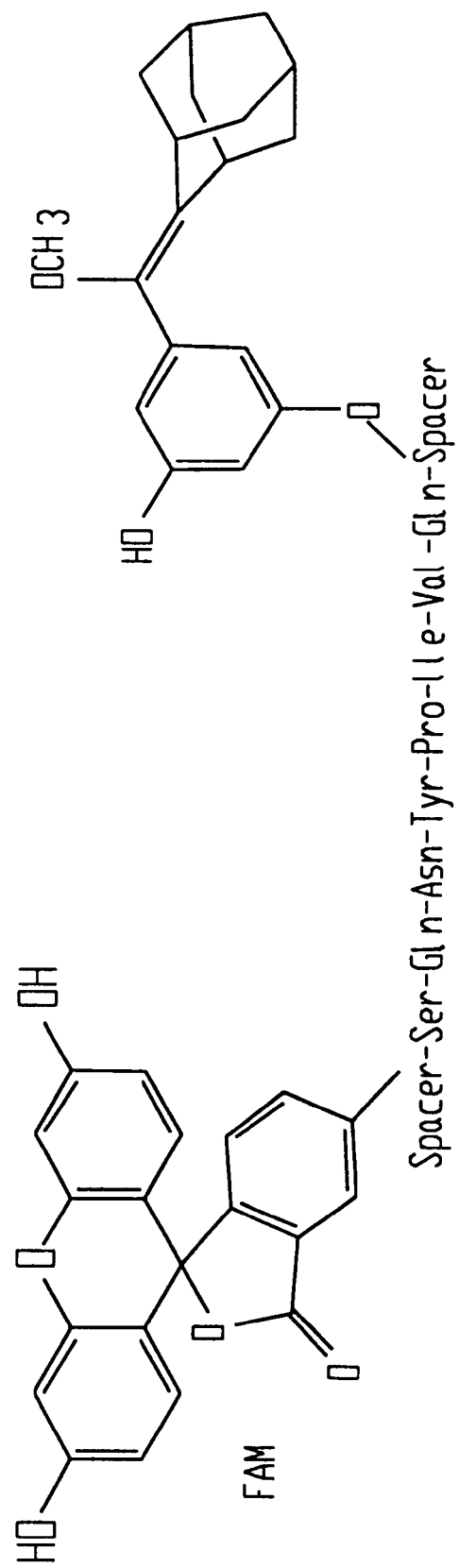
FIG. 14. Synthetic peptide for homogenous assay. This peptide (SEQ ID No:2), also adapted for HIV-1 protease inhibitor detection, is derivatized at both ends of the molecule, in fashion similar to that employed in the heterogenous assay. In this case, however, one terminus, preferably the carboxy terminus, is labeled with an energy accepting fluorescent moiety, such as fluorescein, and the amino terminus is labeled with a 1,2-dioxetane moiety precursor (14A) which can be photooxygenated in situ to the dioxetane (14B). The dioxetane may be triggered by other than chemical (enzymatic or non-enzymatic) means if necessary.
Figure 14B:
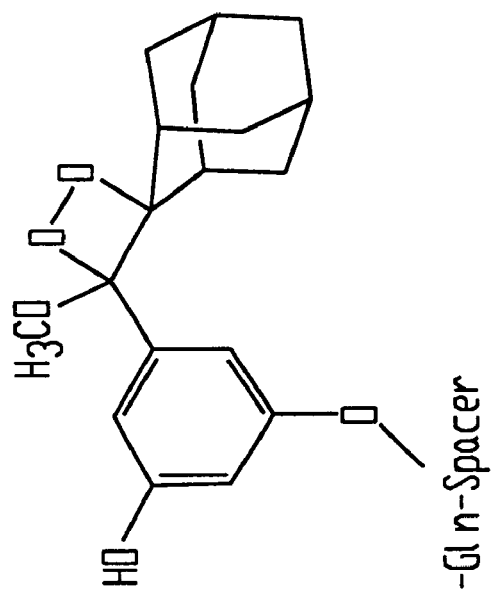
Figure 14B:
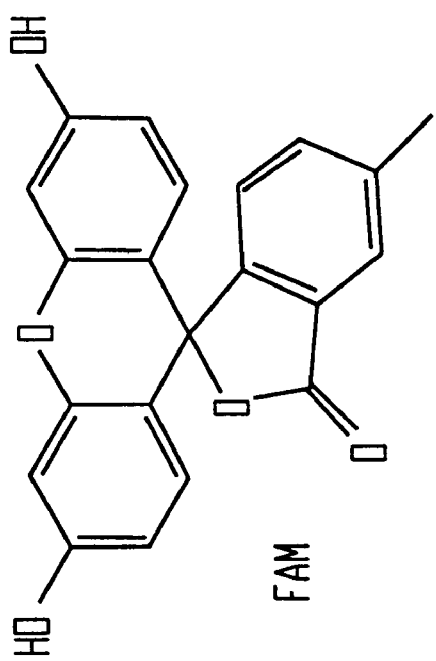

Another approach to a homogeneous assay using an enol lether or dioxetane label is to use a quenching group in place of the fluorescent acceptor. In this format, upon triggering of the dioxetane label, there will be no light from the intact peptide due to the quenching group. If cleavage of the peptide substrate by a protease occurs prior to triggering, emission from the dioxetane group will be observed upon triggering. This quenching process is subject to the same distance restraints as the energy transfer process described above. A suitable quenching group for the substrate shown in FIG. 14 would be a dabcyl group in place of the fluorescein group. Any non-fluorescent light absorbing dye, which has an absorption spectra which overlaps the emission spectra of the donor dioxetane could be used as a quenching group.

Variations on this approach can be made for many types of proteases. Direct covalent or hydrophobic attachment of a peptide substrate to a microwell surface may be required for some proteases. Alternatively, direct synthesis of the peptide on the solid phase may also have advantages.

The heterogenous assay of this invention has been exemplified, below, by reference to an assay adapted to detect inhibition of HIV-1 protease. This example is demonstrative only, and not intended to be limiting.

Materials and Methods

Reagents:
1. The HIV FLAG peptide was custom synthesized by Genemed Synthesis, Inc.
2. Anti-FLAG MI Monoclonal Antibody, FLAG Octapeptide, and Enterokinase were purchased from Eastman Kodak Company.

Neutravidin Coated Plates:
Neutravidin™ Biotin Binding Protein (PIERCE) was diluted to 5 ug/ml or 0.1 ug/ml in BupHTM Carbonate-Bicarbonate buffer (PIERCE), 1 mg/ml BSA (fraction V Sigma) and 100 ul added to white 96 well plates (Dynatech-Microlitel) and incubated for 2 hours at 37° C. The wells were then washed with PBS, 0.1% (v/v) TWEEN-20 and blocked with PBS, 0.1% (V/V) Tween 20, 1 mg/ml BSA overnight at 4 degrees.

Protease Assays:
Rec HIV-PR1 (affinity purified -BACHEM) was diluted in 0.1M NaAcetate, 1M NaCl, 1 mM EDTA, 1 mM DTT, 1 mg/ml BSA, pH 4.7 or pH 5.5 and added to Neutravidin coated plates. Rec HIV-1 inhibitor (Acetyl-pepstatin (BACHEM)), compounds from plate-1001 (Sigma Drug Standards) and/or DMSO was added followed with a 5 minute preincubation before the addition of HIV-1 peptides I or II, (FAM-spacer-Ser-Gln-Asn-Tyr-Pro-lle-Val-Gln-spacer-Biotin (Perkin-Elmer) (SEQ ID No:2) or (FLAG-Ser-Nle-Ala-Glu-Phe-Leu-Val-Arg-Ala-Lys-His-Spacer-Biotin) (SEQ ID No:3) or DABCYL-y-Abu-Ser-Gln-Asn-Tyr-Pro-lle-Val-Gln-EDANS (BACHEM) (SEQ ID No:4) (prior art) respectively. Reactions were done at ambient and/or 37° C. For HPLC analysis, reactions were stopped with 0. 1% TFA and placed on ice before injection. Assays with the BACHEM fluorogenic substrate were measured directly on a LS50B fluorescence spectrophotometer (Perkin-Elmer). Neutravidin coated assay plates with captured biotinylated-fluorescein labeled peptide I were washed with PBS, 0.1% (V/V) Tween20, 1 mg/ml BSA and incubated for 60 min. with anti-fluorescein-alkaline phosphatase Fab fragments (Boehringer Mannheim) at ambient temperature. Plates were washed again with PBS buffer followed by a 10 mM Tris-HCL, 1 mM $MgCl_2$ pH 9.8 wash. 100 ul of CSPD/Sapphire II™ ready to use alkaline phosphatase was added and emitted light was measured in a TR717® microplate luminometer(Tropix).

HPLC Analysis:
Analytical HPLC on the HIV-1 protease substrate cleavage products was done on a Perkin-Elmer UV/V is detector with series 2001c pump, Perkin-Elmer pecosphere 5 C18, 5 um, 4.6 mm×15 cm, gradient of water(0. 1% TFA) and CH$_3$CN (0.1% TFA) from 30% to 60% over 10 minutes at 1 ml/min.

Additions and dilutions were made with a Zymark RapidPlate-96 pipeting station (Zymark Corp.) and washes were done with a Tecan 96PW washer (Tecan).

The present inventors have successfully developed an automated screening assay as shown below to search for novel HIV-1 protease inhibitors.

AUTOMATION STEPS

| # | DESCRIPTION | VOLUME (μL) | AUTOMATION COMPONENT | TIME (MIN) |
|---|---|---|---|---|
| 1 | Add protease buffer containing 50 nM HIV-1 protease | 50 μL | Zymark Rapid plate 96-well pipettor | 1 min |
| 2 | Add test compound | 5 μL | Zymark Rapid plate 96-well pipettor | 1 min |
| 3 | Add HIV Perkin Elmer peptide @ 444 nM | 45 μL | Zymark Rapid plate 96-well pipettor | 1 min |
| 4 | Incubate (32° C.) | | | 60 min |
| 5 | Wash | 3 × 100 μL | Tecan 96PW washer | 0.75 min |
| 6 | Add Anti-Fluorescein-AP conjugate | 100 μL | Zymark Rapid plate 96-well pipettor | 1 min |
| 7 | Incubate (Room Temp.) | | | 30–60 min |
| 8 | Wash | 5 × 100 μL | Tecan 96PW washer | 1 min |
| 9 | Add CSPD + Sapphire II | 100 μL | Zymark Rapid plate 96-well pipettor | 1 min |
| 10 | Read plate | | Tropix TR717 Luminometer | 30 min + 1.4 min |

Figure 6:
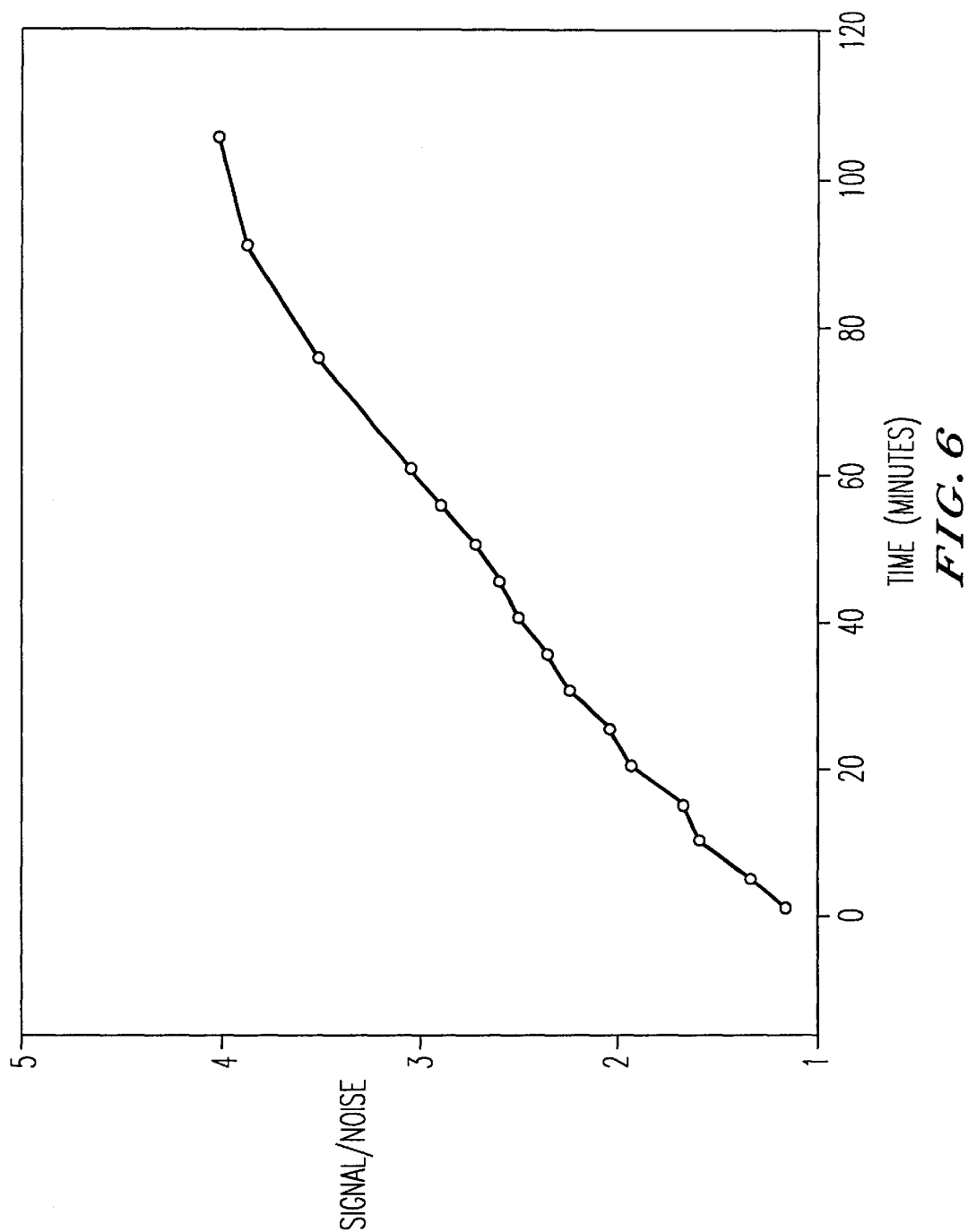
FIG. 6. Hydrolysis of EDANS/DABCYL HIV-1 protease Prior Art Substrate by rec HIV-1 protease. Fluorogenic HIV-1 peptide II was added to protease buffer pH 4.7 in 96 well plates. Rec HIV-1 protease was added at ambient temperature and immediately read over a 105 minute time period on a LS50B fluorescence spectrophotometer (Perkin-Elmer). Excitation was set at 340 nm and emission was set at 490 nm.
Figure 7A:
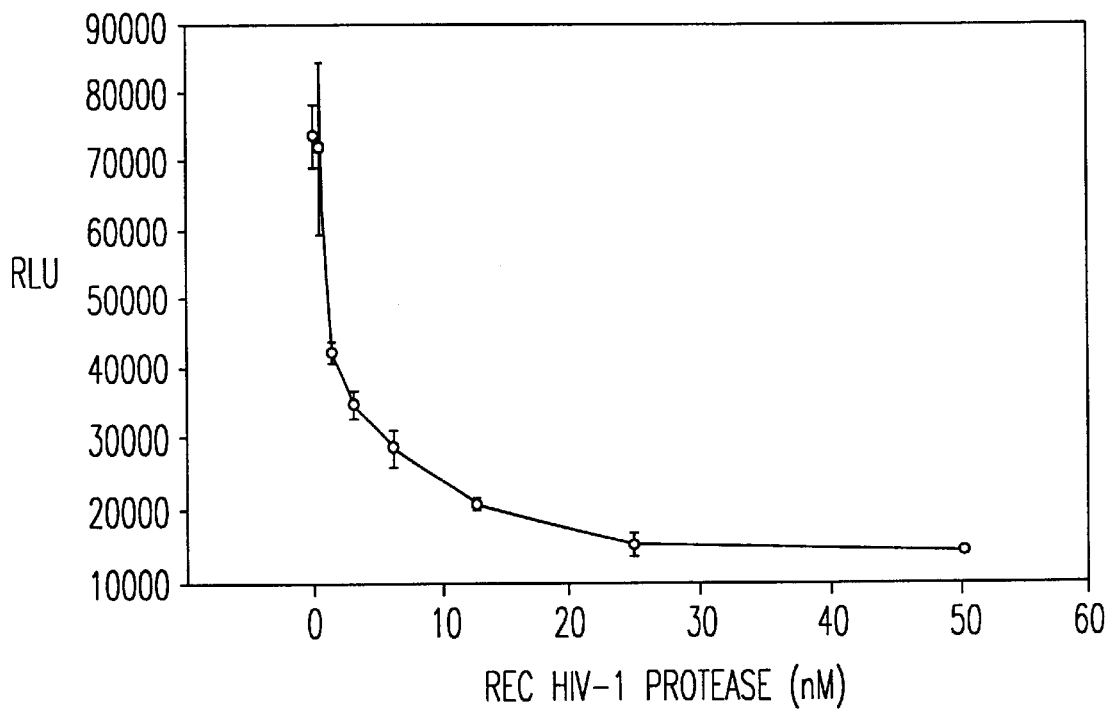
FIG. 7. Hydrolysis and capture of HIV-1 protease substrate I on Neutravidin coated plates. Dilutions of rec HIV-1 protease diluted in protease buffer pH 5.5 were added to wells previously coated with 0.1 ug/ml Neutravidin. 10 pmoles of protease substrate was added to start the reaction and the plate was incubated for 1 hour at 37° C. After a wash step, captured peptide was detected with anti-fluorescein conjugated alkaline phosphatase antibody followed by another wash step and then the addition of CSPD/Sapphire II. Light emission was measured in a TR717 microplate luminometer(Tropix). 100% cleavage of the substrate is not obtained for substrate 1. The date has been adjusted to reflect this phenomenon. In actuality, the detected background may be different.
Figure 7B:
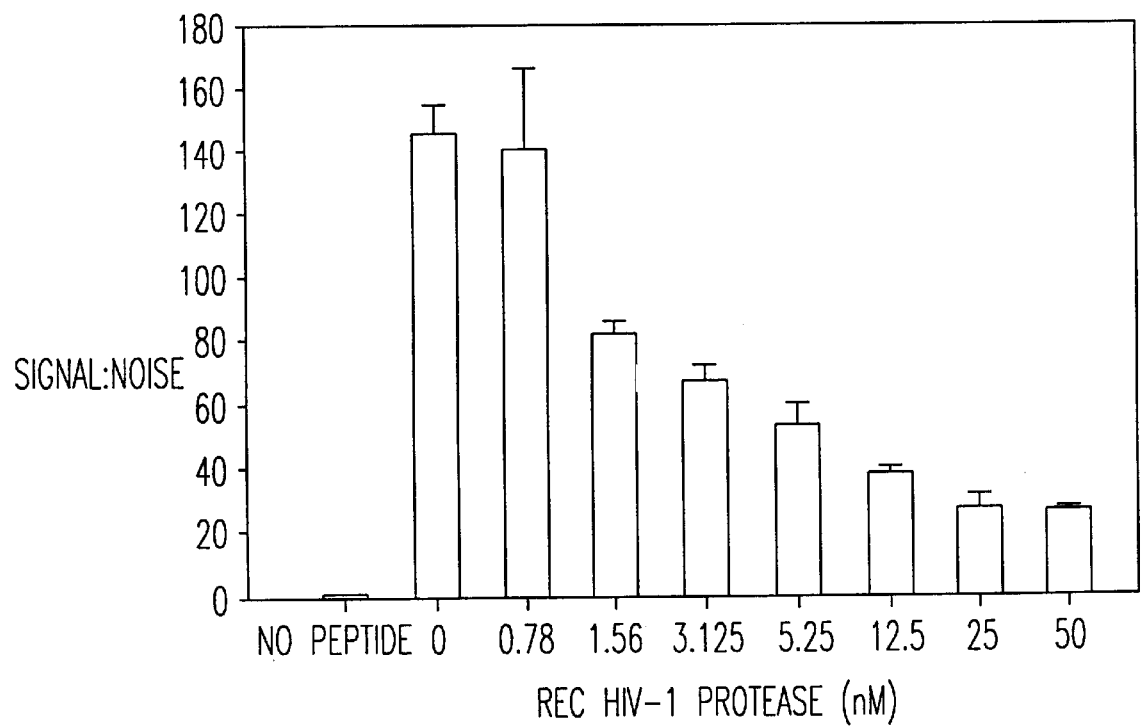
Figure 8:
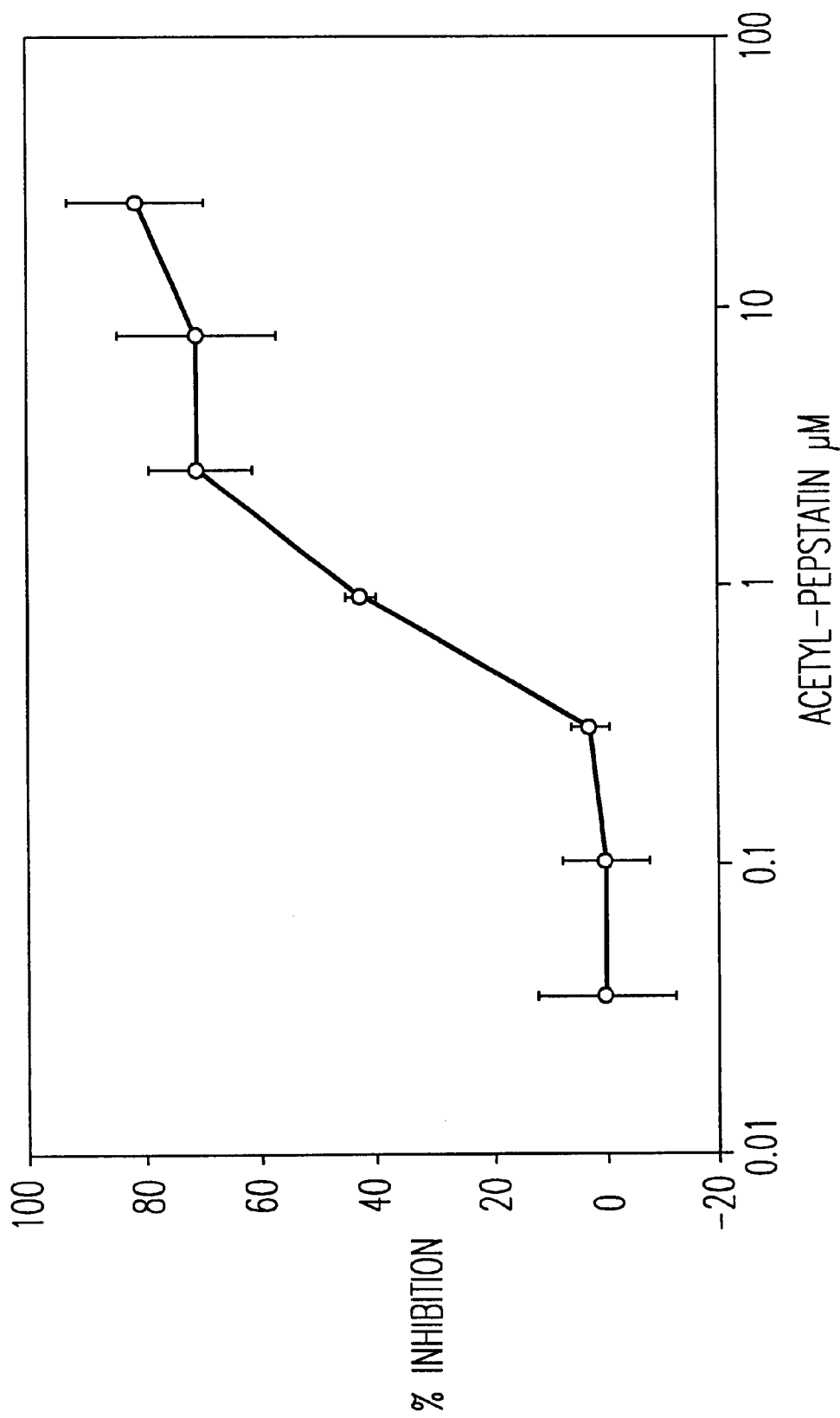
FIG. 8. Rec HIV-1 protease inhibition by acetyl-pepstatin in a HIV-1 capture assay. 2.5 pmoles of rec HIV-1 protease diluted in protease buffer pH 5.5 was added to Neutravidin (0.1 ug/rnl) coated wells. Dilutions of acetyl-pepstatin in DMSO were added to wells followed with a preincubation of 5 minutes. 20 pmoles of HIV-1 protease substrate was added and the plate incubated for 1 hour at 37° C. After a wash step captured peptide was detected with an anti-fluorescein conjugated alkaline phosphatase antibody. After a second wash step, CSPD/Sapphire II was added and light emission was measured in a TR717 microplate luminometer (Tropix).
Figure 9:
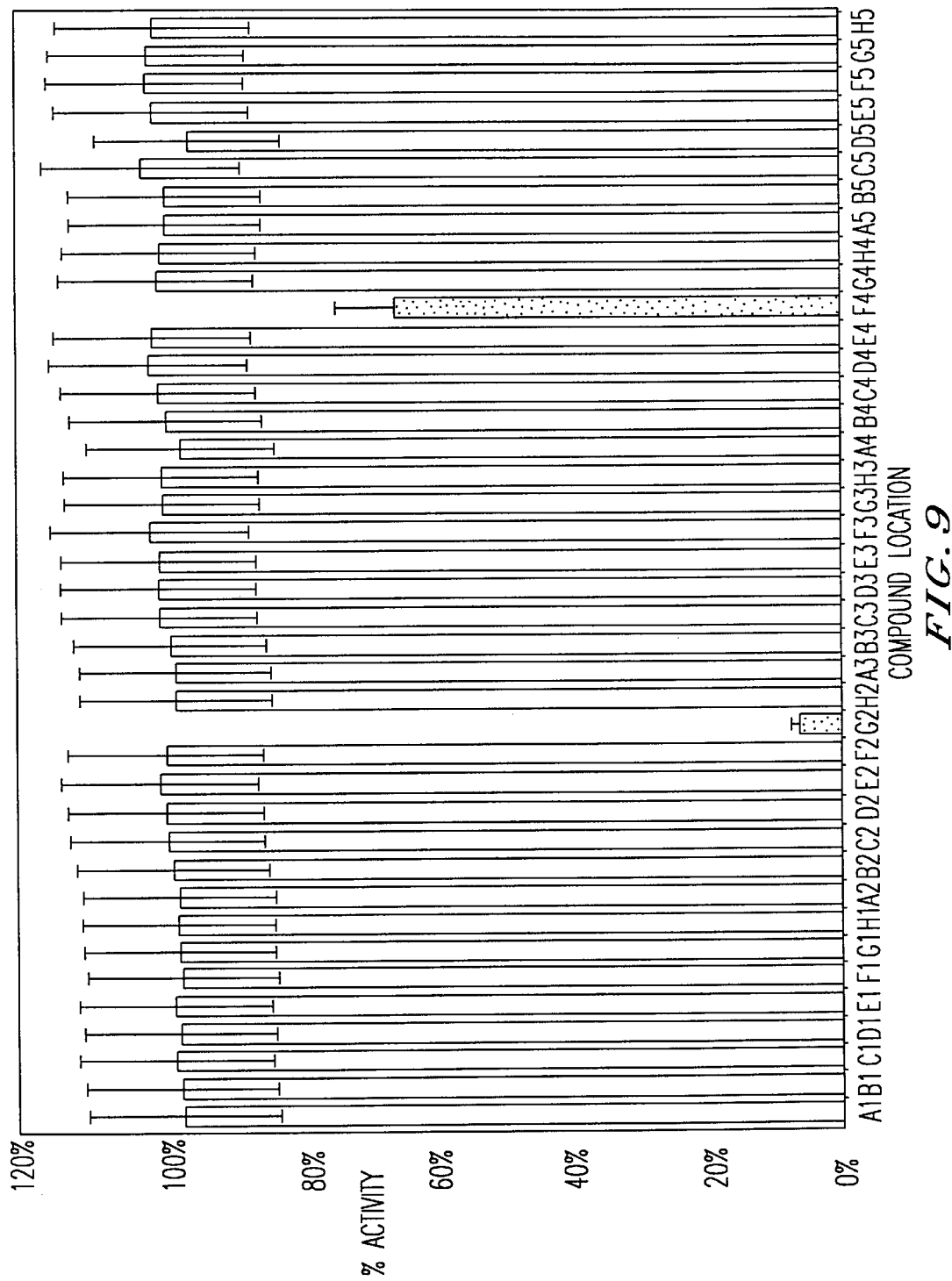
FIG. 9. Screening compound plate-1001 at 25 uM (5% DMSO) for rec HIV-1 protease inhibition. 2.5 pmoles of rec HIV-1 protease diluted in protease buffer pH 5.5 was added to Neutravidin coated plates. 5 ul from a compound screening plate largely composed of drug standards was added and preincubated for 5 minutes. 20 pmoles of HIV-1 protease substrate I was added and the plate was incubated for 60 minutes at 37° C. After a wash step, captured peptide was detected with anti-fluorescein conjugated alkaline phosphatase antibody. After a second wash step, CSPD/Sapphire II was added and light emission was measured in a TR717 microplate luminometer(Tropix).
Figure 10A:
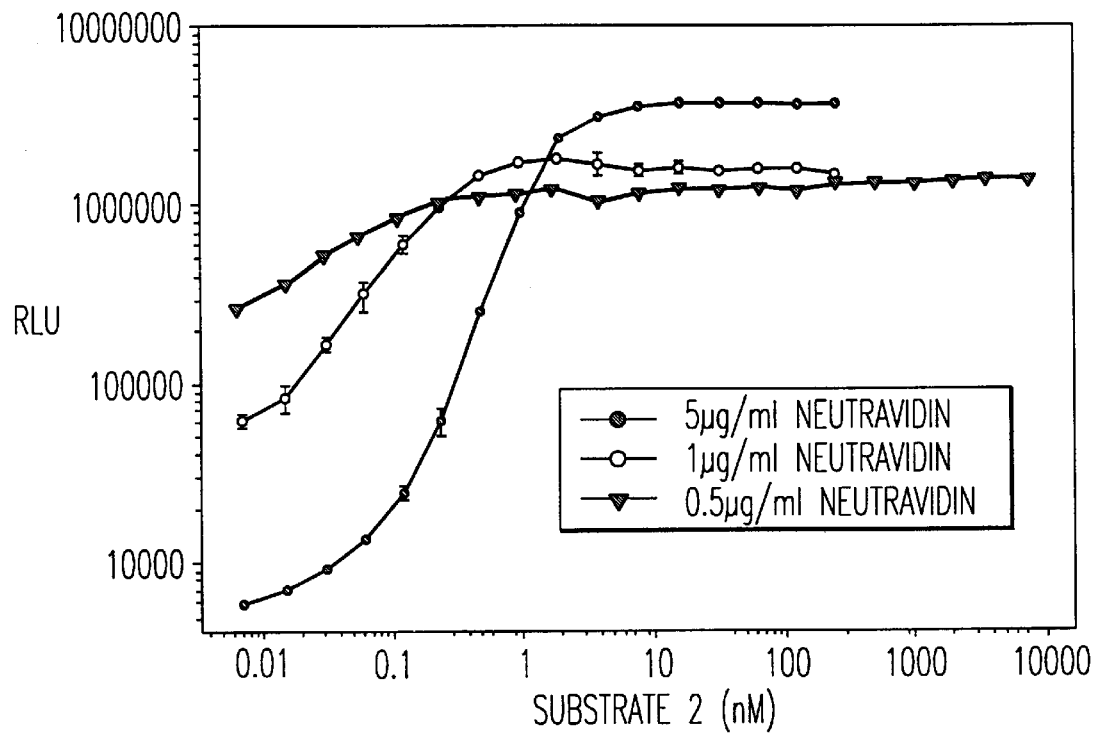
FIG. 10. HIV FLAG Peptide titration on Neutravidin and Anti-FLAG MI monoclonal antibody coated plates. 100 ul of diluted HIV FLAG peptide was added to various densities of pre-coated Neutravidin or Anti FLAG MI monoclonal antibody coated plates. Coating was achieved by diluting a given amount of Neutravidin or Anti-FLAG MI monoclonal antibody and BSA in PBS so as to achieve a total protein concentration of 5 $\mu$g/ml. Plates were incubated for 1 hour at 37° C. followed by a 3x wash with TBS/0.05% Tween/3 mM $CaCl_2$. 100 ul of a 1:20,000 dilution of Avidix-AP was added and incubated for 1 hour at room temp. After 3 washes in TBS/Tween/$CaCl_2$ buffer and 1 wash with 1x Tris/1 mM MgCl/3 mMCaCl pH 9.8, 100 ul ready to sue CSPD/Sapphire II was added and wells incubated for 30 min at room temp. Luminescence was then measured in a TR717 microplate luminometer (Tropix). The present inventors have discovered novel peptide capture conditions which permit the assay to be performed as a single well (plate) assay as opposed to a 2 step transfer and dilution assay.
Figure 10B:
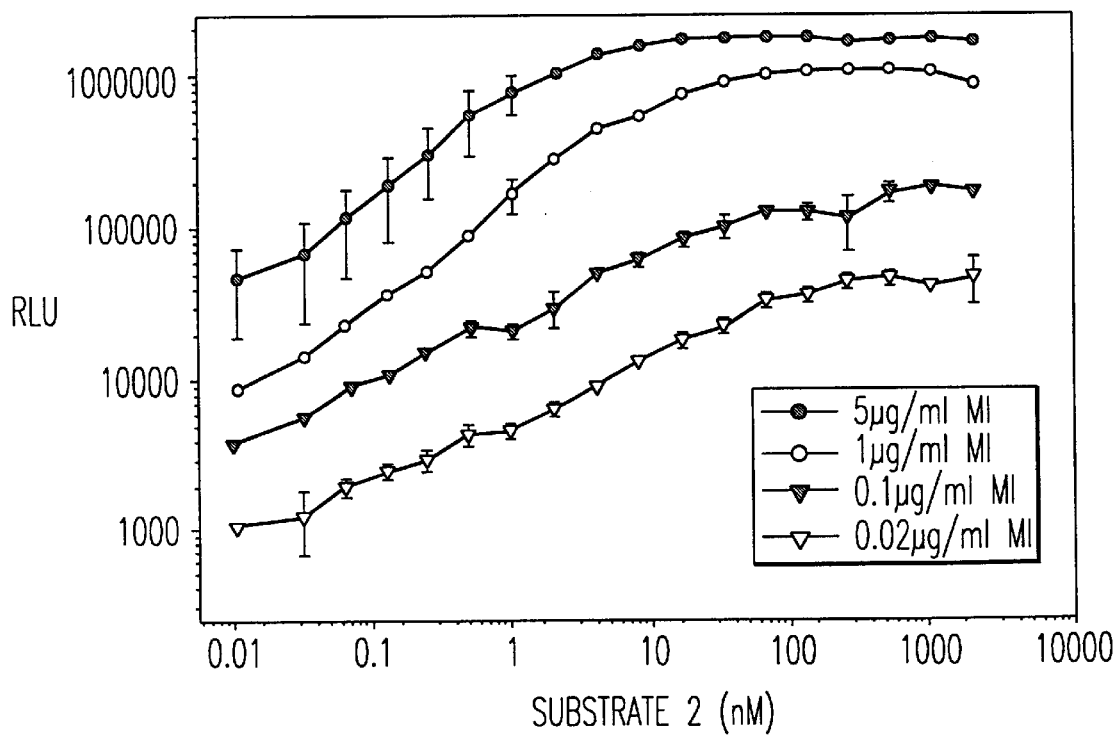
Figure 11:
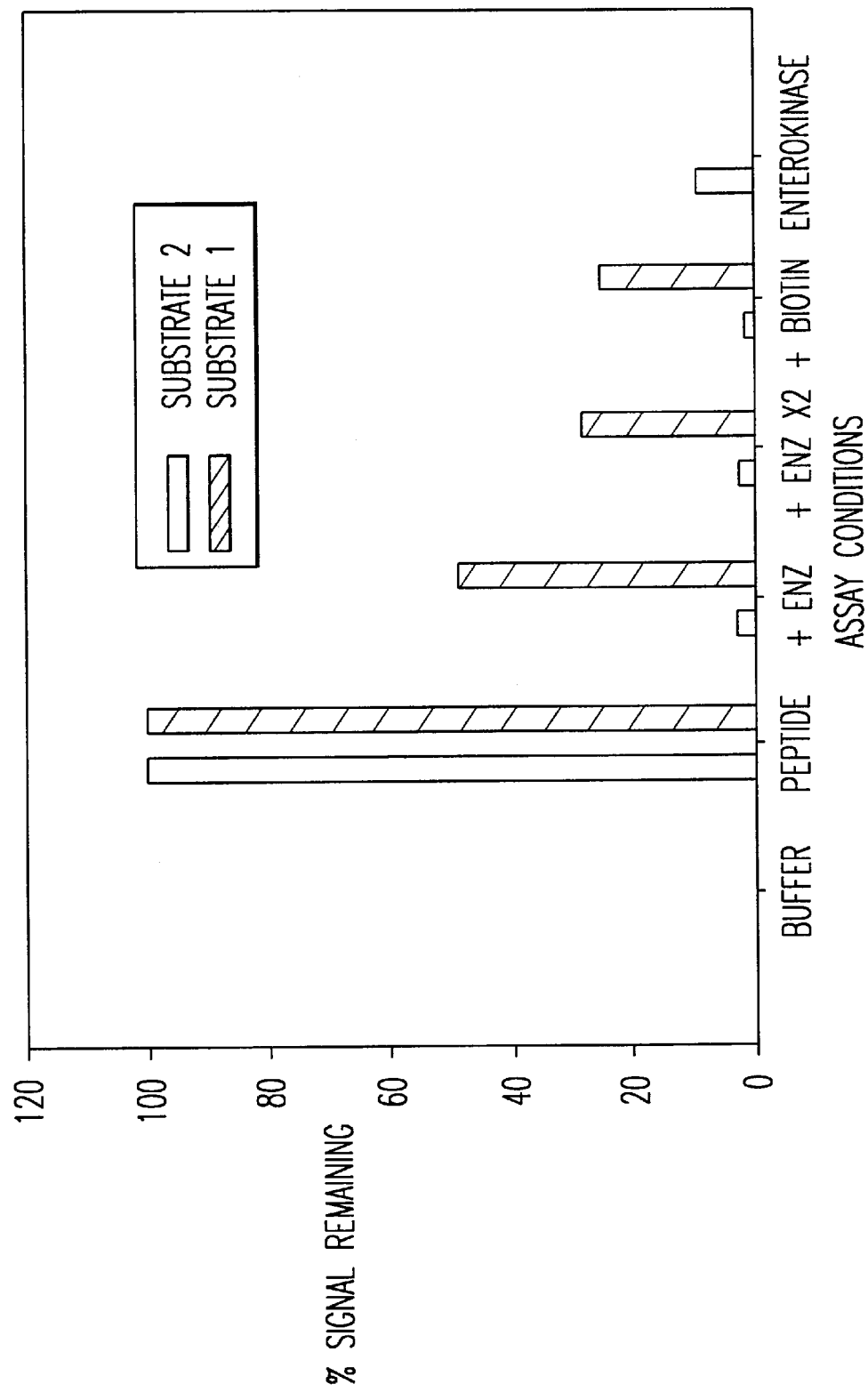
FIG. 11. Capture of HIV FLAG and HIV FAM Peptides on Neutravidin (5 ug/ml) coated plates post hydrolysis with rec HIV-1 protease (50 nM). 50 nM rec HIV-1 protease was added to 1 uM HIV FLAG or HIV FAM peptides in protease buffer (0.1 nM NaAcetate, 1M NaCl, 1 mM EDTA, 1 mM DTT, 1 mg/ml BSA, pH 4.7). Biotin at 0.5 mM and 5 Units of enterokinase were added to control tubes. Reactions were done for 1 hour at 37° C. in eppendorf tubes. All tubes were then placed on ice to stop the reaction. An additional 5OnM rec HIV-1 protease was added to 2 of the reaction tubes and incubated further for 30 minutes at 37° C. HIV FLAG peptide containing tubes were diluted 1:100 (10 nM final) and HIV FAM peptide tubes were diluted 1:100,000 (0.1 nM final) in protease buffer. 100 ul was added to Neutravidin coated wells (5 ug/ml) and incubated for 1 hour at room temp. Wells were then washed with 3x PBS/Tween/CaCl buffer. 100 ul of 1:5000 dilution of Anti FITC-AP Fab Fragment was added to HIV FAM peptide containing wells and 100 ul of a precomplexed Anti-FLAG MI antibody (1:1000) and Goat anti mouse-AP conjugate (1:10,000) was added to HIV FLAG peptide containing wells. Plates were incubated for additional hour at room temp then washed 3x in TBS/Tween/CaCl and 1x Tris/MgCl/CaCl pH 9.8. 100 ul ready to use CSPD/Sapphire II was added to wells and incubated 30 minutes at room temp. Luminescence was then measured in a TR717 microplate luminometer.
Figure 12:
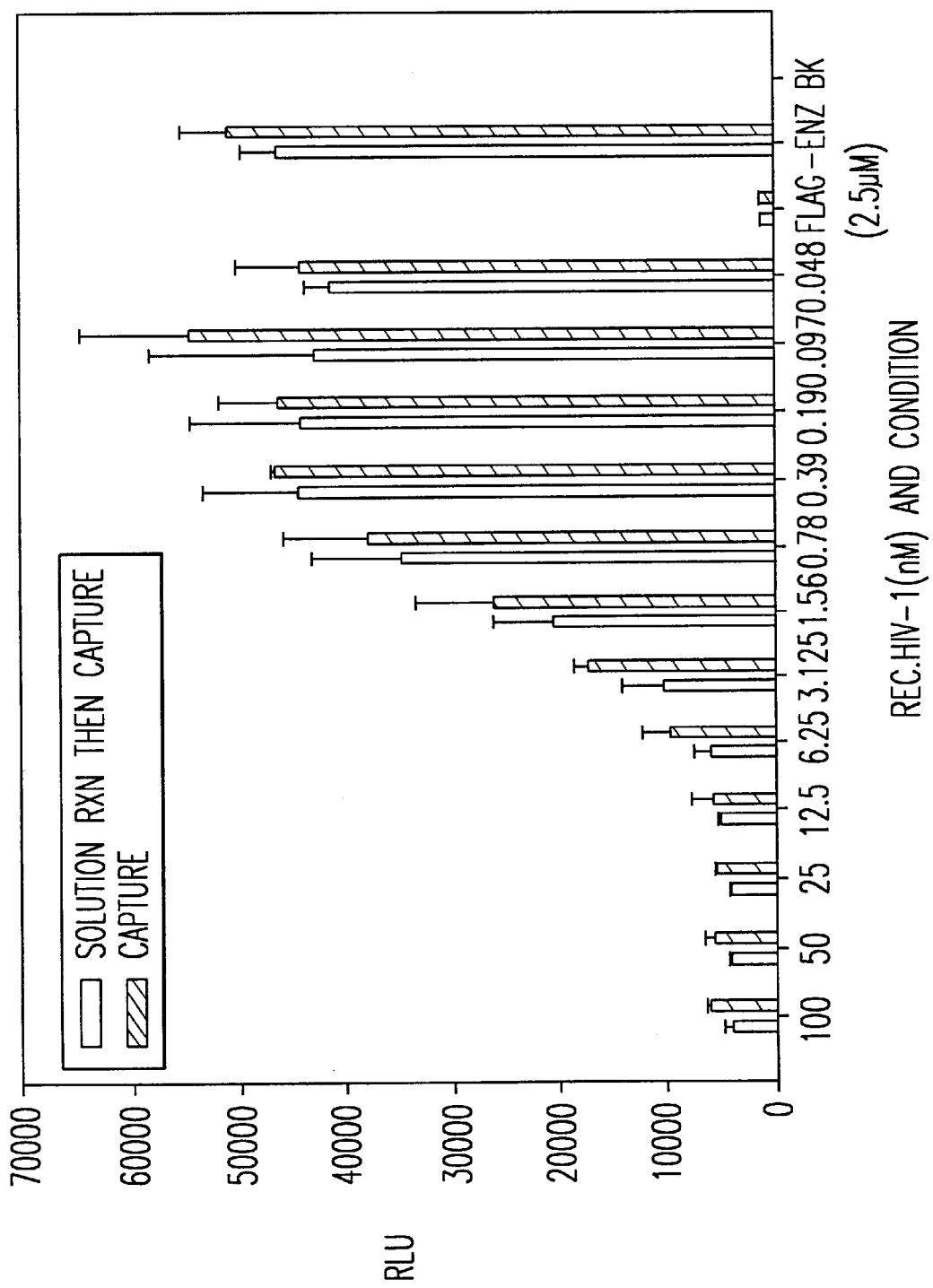
As shown in FIG. 12, the signals are relatively the same when done as a one step or two step assay suggesting that non-specific cleavage of other assay components by the rec HIV-1 protease is nonexistent.
Figure 13:
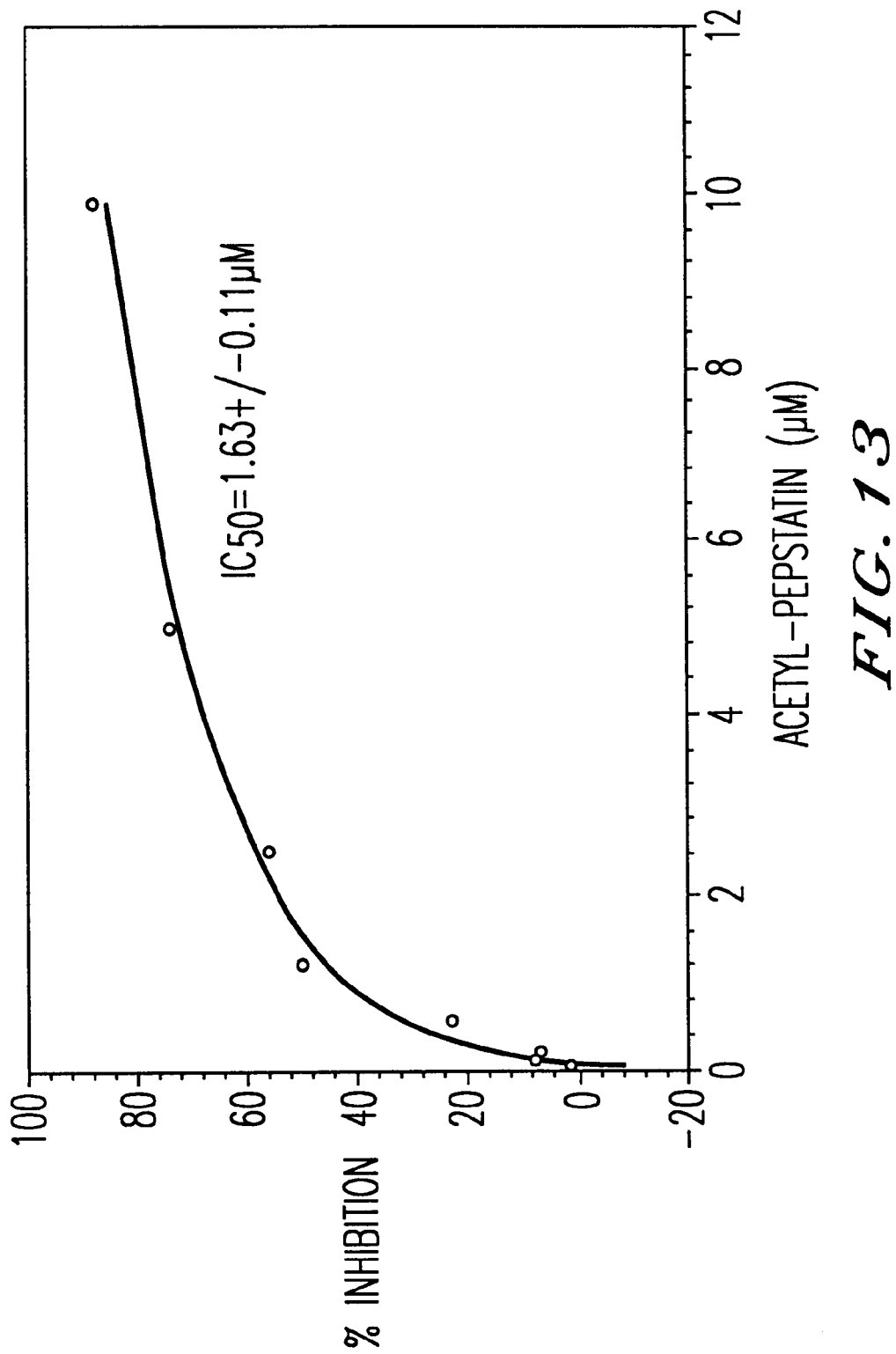
FIG. 13. Inhibition of 12.5 nM rec HIV-1 Protease with Acetyl-Pepstatin. Assays consisted of reactions with 100 nM HIV FLAG Peptide in wells coated with Anti-FLAG MI antibody (0.1 ug/ml) for 1 hour at 37° C. Dilutions of acetyl-pepstatin were preincubated for 5 minutes with rec HIV-1 enzyme before adding to HIV FLAG peptide substrate in protease buffer. All additions were made on a Zymark Rapid Plate. The plate was then washed 4x with TBS/3 mM $CaCl_2$/0.05% Tween on Tecan 96 plate washer. 100 ul of a 1:20,000 dilution of Avidix-AP conjugate was added to each well and incubated for 1 hour @ room temp. The plate was then washed 3x with above buffer and 1x with Tris/MgCl/CaCl pH 9.8. 100 ul CSPD/Sapphire II was added, incubated for 30 min and then light emission was measured in a TR717 luminometer (Tropix). Note: Acetyl-pepstatin is a well known aspartic proteinase inhibitor and is a reported inhibitor of HIV-1 protease (*Pro. Natl. Sci. U.S.A.* 85, 66123, (1988)).

We have shown that this protease assay can be set up as an endpoint capture assay th minimal reagent use. An HIV-1 peptide substrate I concentration of 200 nM and a rec HIV-1 protease concentration of 25–50nM have been shown to be optimal working concentrations with good sensitivity and acceptable signal:noise. A resonance energy tansfer assay reported by Abbott Laboratories, Matayoshi, E. D. et al., Science 247: 954–958 (1990), utilizes micromolar amounts of HIV-1 peptide II. This assay is reported as an assay with a linear detection window of less than 5 minutes, which we have found to have a poor signal to noise ratio making it a difficult robotic assay to automate. FIG. 6. This assay gave a maximum s/n ratio of 4, while the inventive assay gives a s/n ratio of greater than 140 when using the FLAG/anti-FLAG ligand binding pair. By utilizing common laboratory reagents such as biotin and fluorescein one can eliminate the need to generate sequence specific monoclonal antibodies as described in the alternative HIV peptide capture based assay by Fournout, S. et al., Anal. Chem. 69, 1746–1752 (1997). We have shown that DMSO is well tolerated in the assay. The IC$_{50}$ of acetyl-pepstatin in our capture assay was 2–3 uM compared to 0.3 uM reported by Fournout, S. et al.

This invention has been disclosed in terms of both generic description and specific example. Variations will occur to those of ordinary skill in the art, including peptide moiety identities, specific proteolytic enzymes to be employed, enhancement agents and enhancement additives, and specific assay formats without the exercise of inventive faculty. Such variations remain within the scope of the invention, save for variations excluded by the recitation of the claims presented below.

---

What is claimed is:

1. A method for conducting an assay to determine whether a target compound exhibits activity as a protease inhibitor, comprising:

(a) combining a protease and said target compound in an environment further comprising a construct, wherein said environment is such that said protease cleaves said construct in the absence of inhibition of said protease, said construct comprising an amino acid sequence capable of being cleaved by said protease terminating (1) at a first end with a first member of a first ligand binding pair and (2) at a second end with a first member of a second ligand binding pair, wherein
   said first member of said first ligand binding pair binds to a second member of said first ligand binding pair, said second member of said first ligand binding pair is bound to a surface, (b) removing any fragments of said construct cleaved by said protease, (c) after step (a), adding a second member of said second ligand binding pair complexed with an enzyme and allowing said second member of said second ligand binding pair to bind to said first member of said second ligand binding pair, (d) removing any unbound second member of the second ligand binding pair complexed with the enzyme, and (e) adding a 1,2-dioxetane which is a substrate for said enzyme and observing chemiluminescence released thereby, wherein emission of said chemiluminescence is indicative of protease inhibition activity by said target compound.

2. The method of claim 1, wherein said chemiluminescence permits determination of a degree of inhibitory activity exhibited by said compound.

3. The method of claim 1, wherein said assay is a transfer free single plate endpoint assay.

4. The method of claim 1, wherein said surface is at least a portion of at least one well of a test plate.

5. The method of claim 1, wherein said second member of said second ligand binding pair is an antibody.

6. The method of claim 1, wherein said first ligand binding pair is biotin and a compound which binds to biotin at least as tightly as avidin.

7. The method of claim 1, wherein said second ligand binding pair is biotin and a compound which binds to biotin at least as tightly as avidin.

8. The method of claim 6, wherein said compound which binds to biotin at least as tightly as avidin is avidin or strepavidin.

9. The method of claim 7, wherein said compound which binds as tightly as avidin is avidin or strepavidin.

10. The method of claim 1, wherein said first member of said first ligand binding pair is biotin and said first member of said second ligand binding pair is fluorescein.

11. The method of claim 1, wherein said second ligand binding pair is an eight amino acid peptide (Asp-Tyr-Lys-Asp-Asp-Asp-Asp-Lys) known as FLAG and an antibody therefor.

12. The method of claim 1, wherein said protease is selected from the group consisting of a serine protease, a cysteine protease, an aspartic protease and a metallo proteinase.

13. The method of claim 1, wherein said protease is selected from the group consisting of human immunodeficiency virus 1 (HIV-1 protease), caspases, cathhepsins, hydrolase, L-proteinase, calpain, interleukin converting proteases, urokinase, trypsin, thrombin, HIV-2 protease, Yapsin I, Yapsin 3, Plasmepsin I, Plasmepsin II, collagenase, gelatinases, stromelysin, amino peptidase and elastase.

14. The method of claim 13, wherein said protease is HIV-1 protease.

* * * * *

SEQUENCE LISTING

<160> NUMBER OF SEQ ID NOS: 6

<210> SEQ ID NO: 1
<211> LENGTH: 5
<212> TYPE: PRT
<213> ORGANISM: Artificial Sequence
<220> FEATURE:
<221> NAME/KEY: UNSURE
<222> LOCATION: (1)
<223> OTHER INFORMATION: May be Ser or Thr.
<220> FEATURE:
<221> NAME/KEY: UNSURE
<222> LOCATION: (2)
<223> OTHER INFORMATION: May be any amino acid.
<220> FEATURE:
<221> NAME/KEY: UNSURE
<222> LOCATION: (3)
<223> OTHER INFORMATION: May be any amino acid.
<220> FEATURE:
<221> NAME/KEY: UNSURE
<222> LOCATION: (4)
<223> OTHER INFORMATION: May be Tyr or Phe.
<220> FEATURE:
<223> OTHER INFORMATION: Description of Artificial Sequence:Conserved
      sequence for detecting protease inhibitors.

<400> SEQUENCE: 1

Xaa Xaa Xaa Xaa Pro
 1               5

```
<210> SEQ ID NO: 2
<211> LENGTH: 8
<212> TYPE: PRT
<213> ORGANISM: Artificial Sequence
<220> FEATURE:
<221> NAME/KEY: UNSURE
<222> LOCATION: (1)
<223> OTHER INFORMATION: May be modified with fluorescein-spacer.
<220> FEATURE:
<221> NAME/KEY: UNSURE
<222> LOCATION: (8)
<223> OTHER INFORMATION: May be modified with spacer-biotin-NH2 or
      spacer-biotin.
<220> FEATURE:
<223> OTHER INFORMATION: Description of Artificial Sequence:Conserved
      sequence for detecting protease inhibitors.

<400> SEQUENCE: 2

Ser Gln Asn Tyr Pro Ile Val Gln
  1               5

<210> SEQ ID NO: 3
<211> LENGTH: 11
<212> TYPE: PRT
<213> ORGANISM: Artificial Sequence
<220> FEATURE:
<221> NAME/KEY: UNSURE
<222> LOCATION: (1)
<223> OTHER INFORMATION: May be modified by FLAG.
<220> FEATURE:
<221> NAME/KEY: UNSURE
<222> LOCATION: (11)
<223> OTHER INFORMATION: May be modified by spacer-biotin.
<220> FEATURE:
<221> NAME/KEY: MOD_RES
<222> LOCATION: (2)
<223> OTHER INFORMATION: Nle.
<220> FEATURE:
<223> OTHER INFORMATION: Description of Artificial Sequence:Conserved
      sequence for detecting protease inhibitors.

<400> SEQUENCE: 3

Ser Xaa Ala Glu Phe Leu Val Arg Ala Lys His
  1               5                  10

<210> SEQ ID NO: 4
<211> LENGTH: 8
<212> TYPE: PRT
<213> ORGANISM: Artificial Sequence
<220> FEATURE:
<221> NAME/KEY: CONFLICT
<222> LOCATION: (1)
<223> OTHER INFORMATION: May be modified by DABCYL-y-Abu.
<220> FEATURE:
<221> NAME/KEY: UNSURE
<222> LOCATION: (8)
<223> OTHER INFORMATION: May be modified by EDANS.
<220> FEATURE:
<223> OTHER INFORMATION: Description of Artificial Sequence:Conserved
      sequence for detecting protease inhibitors.

<400> SEQUENCE: 4

Ser Gln Asn Tyr Pro Ile Val Gln
  1               5

<210> SEQ ID NO: 5
<211> LENGTH: 8
<212> TYPE: PRT
<213> ORGANISM: Artificial Sequence
<220> FEATURE:
<221> NAME/KEY: UNSURE
<222> LOCATION: (1)
```

```
-continued

<223> OTHER INFORMATION: May be modified by Fluorescein-spacer.
<220> FEATURE:
<221> NAME/KEY: UNSURE
<222> LOCATION: (8)
<223> OTHER INFORMATION: May be modified by spacer-biotin.
<220> FEATURE:
<223> OTHER INFORMATION: Description of Artificial Sequence:Conserved
      sequence for detecting protease inhibitors.

<400> SEQUENCE: 5

Ser Glu Asn Tyr Pro Ile Val Glu
  1               5

<210> SEQ ID NO: 6
<211> LENGTH: 8
<212> TYPE: PRT
<213> ORGANISM: Artificial Sequence
<220> FEATURE:
<223> OTHER INFORMATION: Description of Artificial Sequence:Conserved
      sequence for detecting protease inhibitors.

<400> SEQUENCE: 6

Ser Gln Asn Tyr Pro Ile Val Gln
  1               5
```